US006862403B2

(12) United States Patent
Pedrotti et al.

(10) Patent No.: US 6,862,403 B2
(45) Date of Patent: Mar. 1, 2005

(54) ROTATABLE PLUG ASSEMBLY INCLUDING AN EXTRA OUTLET

(75) Inventors: Andrea Pedrotti, Pietramurata (IT); Paolo Campedelli, Mori (IT); Stefano Baldessari, Caldonazzo (IT)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/359,097

(22) Filed: Feb. 6, 2003

(65) Prior Publication Data

US 2003/0194225 A1 Oct. 16, 2003

Related U.S. Application Data

(63) Continuation-in-part of application No. 10/212,746, filed on Aug. 7, 2002.
(60) Provisional application No. 60/371,162, filed on Apr. 10, 2002.

(30) Foreign Application Priority Data

Aug. 7, 2001 (EP) .............................................. 01830528

(51) Int. Cl.⁷ ................................................. F24F 6/08
(52) U.S. Cl. ....................................... 392/395; 392/392
(58) Field of Search ................................. 392/386, 387, 392/390, 392, 393, 395; 122/306; 239/34, 44, 45, 135, 136; 337/186, 197, 198, 255, 259, 269

(56) References Cited

U.S. PATENT DOCUMENTS

| 2,305,101 | A |   | 12/1942 | O'Brien |           |
|-----------|---|---|---------|---------|-----------|
| 2,582,800 | A | * | 1/1952  | Sorenson | ...... 439/30 |
| 2,611,068 | A | * | 9/1952  | Wellens | ...... 392/392 |
| 3,123,421 | A | * | 3/1964  | Phillips | ...... 439/17 |
| 3,780,260 | A |   | 12/1973 | Elsner |           |
| 4,743,999 | A |   | 5/1988  | Hames | ...... 361/56 |
| 4,804,821 | A | * | 2/1989  | Glucksman | ...... 392/390 |
| 5,038,394 | A |   | 8/1991  | Hasegawa et al. |   |
| 5,095,647 | A | * | 3/1992  | Zobele et al. | ...... 43/125 |
| 5,554,039 | A |   | 9/1996  | Doudon |           |
| 5,647,053 | A |   | 7/1997  | Schroeder et al. |   |
| D382,658  | S |   | 8/1997  | Yu |                   |
| 5,926,614 | A |   | 7/1999  | Steinel |          |
| 5,937,140 | A |   | 8/1999  | Leonard et al. |   |
| 5,957,701 | A |   | 9/1999  | McMillin |        |
| 6,068,490 | A | * | 5/2000  | Salzberg | ...... 439/25 |
| D433,521  | S |   | 11/2000 | Jaworski |        |
| 6,361,752 | B1| * | 3/2002  | Demarest et al. | ...... 422/306 |
| 6,466,739 | B2| * | 10/2002 | Ambrosi et al. | ...... 392/395 |
| 6,478,440 | B1|   | 11/2002 | Jaworski et al. | |
| 2002/0172512 | A1 | | 11/2002 | Stathakis et al. | |

FOREIGN PATENT DOCUMENTS

| EP | 0 464 451 A1 | 1/1992 |
| EP | 0 962 132 A1 | 12/1999 |
| WO | WO 02/26274 | 4/2002 |

* cited by examiner

Primary Examiner—Sang Y. Paik

(57) ABSTRACT

A wall-mounted, plug-in appliance includes a housing and a plug assembly, which is rotatably disposed within the housing. The plug assembly includes (i) a plug for electrically connecting the plug assembly to a wall outlet and (ii) at least one integral extra outlet to which another electrical appliance can be plugged in. The plug assembly conducts power to electrical components of the appliance at each of at least two 90-degree intervals of rotation of the plug assembly, and the extra outlet is accessible through different ones of a plurality of windows in the housing at different 90-degree intervals of rotation of the plug assembly.

25 Claims, 12 Drawing Sheets

ROTATABLE PLUG ASSEMBLY INCLUDING AN EXTRA OUTLET

RELATED APPLICATIONS

This application is a continuation-in-part of U.S. patent application Ser. No. 10/212,746, filed Aug. 7, 2002. This application also claims the benefit of U.S. Provisional Patent Application No. 60/371,162, filed Apr. 10, 2002.

BACKGROUND OF THE INVENTION

1. Field of the Invention

Our invention relates generally to a rotatable plug assembly for incorporation in an electrical appliance, and, particularly, to a rotatable plug assembly equipped with one or more extra electrical outlets.

2. Description of the Related Art

Plug-in electrical appliances such as vaporizers, night lights, timers, and the like, are well known in the art. Typically, these devices are left plugged into a wall outlet for extended periods of time, thereby preventing or limiting the use of other electrical appliances in the outlet. To address this problem, several patents propose electrical appliances having an extra outlet to replace the one occupied by the plugged-in appliance. U.S. Pat. Nos. 5,937,140 and 6,478,440, each of which is incorporated by reference herein, disclose examples of plug-in appliances with extra outlets.

Some types of plug-in appliances, particularly wick-based liquid vaporizers, must be in an upright orientation in order to work properly. Because some outlets are vertical (i.e., one socket is above another one), while other outlets are horizontal (i.e., side-by-side sockets), it is preferable for these appliances to have a rotatable plug which permits the device to be used in both vertical and horizontal outlets. U.S. Pat. No. 5,647,053, which also is incorporated by reference herein, discloses a wick-based liquid vaporizer having a rotatable plug.

SUMMARY OF THE INVENTION

In one aspect, our invention relates to a wall-mounted, plug-in appliance including a housing and a plug assembly. The plug assembly is rotatably disposed within the housing and includes (i) a plug for electrically connecting the plug assembly to a wall outlet and (ii) at least one integral extra outlet to which another electrical appliance can be plugged in. The plug assembly conducts power to electrical components of the appliance at each of at least two 90-degree intervals of rotation of the plug assembly, and the extra outlet is accessible through different ones of a plurality of windows in the housing at different 90-degree intervals of rotation of the plug assembly.

In another aspect, our invention relates to a wall-mounted, plug-in appliance including a housing and a plug assembly. The plug assembly is rotatably disposed within the housing and includes (i) a set of plug blades, extending in a direction parallel to the axis of rotation of the plug assembly, for electrically connecting the plug assembly to a wall outlet, and (ii) at least one integral extra outlet for receiving a set of plug blades of another electrical device. The extra outlet is oriented such that the plug blades of the other electrical device, when inserted into the extra outlet, extend in a direction substantially perpendicular to the axis of rotation of the plug assembly. The plug assembly electrically connects electrical components of the appliance to the wall outlet at each of four 90-degree intervals of rotation of the plug assembly, and the extra outlet is accessible through different ones of a plurality of windows in the housing at at least two of the four 90-degree intervals of rotation.

In yet another aspect, our invention relates to an electrical plug-in device for dispersing a chemical active into a surrounding environment. The device includes a housing with a plurality of windows, at least one electrical component contained within the housing for enhancing dispersion of the chemical active to the surrounding environment, and a plug assembly rotatably disposed within the housing. The plug assembly includes (i) a plug for electrically connecting the plug assembly to a wall outlet and (ii) at least one integral extra outlet to which another electrical appliance can be plugged in. The plug assembly conducts power to the electrical component at each of at least two 90-degree intervals of rotation of the plug assembly, and the extra outlet is accessible through different ones of the plurality of windows in the housing at different 90-degree intervals of rotation of the plug assembly.

In still another aspect, our invention relates to a plug-in vaporizer for dispersing a chemical active into a surrounding environment. The vaporizer includes (i) a bottle containing a liquid formulation including at least one chemical active, (ii) a wick, having a lower portion disposed within the bottle and an upper portion protruding from the bottle, for drawing the liquid formulation from the bottle toward the upper portion of the wick, (iii) a housing in which the bottle is detachably retained, the housing including a plurality of windows, (iv) an electrical heating device, disposed within the housing at a position proximate to the upper portion of the wick, for enhancing evaporation of the liquid formulation from the upper portion of the wick, and (v) a plug assembly rotatably disposed within the housing for supplying power to the heating device. The plug assembly includes a set of plug blades, extending in a direction parallel to the axis of rotation of the plug assembly, for electrically connecting the plug assembly to a wall outlet, and at least one integral extra outlet for receiving a set of plug blades of another electrical appliance. The extra outlet is oriented such that the plug blades of the other electrical appliance, when inserted into the extra outlet, extend in a direction substantially perpendicular to the axis of rotation of the plug assembly. The plug assembly electrically connects the electrical components of the appliance to the wall outlet at each of four 90-degree intervals of rotation of the plug assembly, and the extra outlet is accessible through different ones of the plurality of windows in the housing at at least two of the four 90-degree intervals of rotation.

A better understanding of these and other features and advantages of our invention may be had by reference to the drawings and to the accompanying description, in which preferred embodiments of the invention are illustrated and described.

DESCRIPTION OF THE PREFERRED EMBODIMENTS

Figure 1:
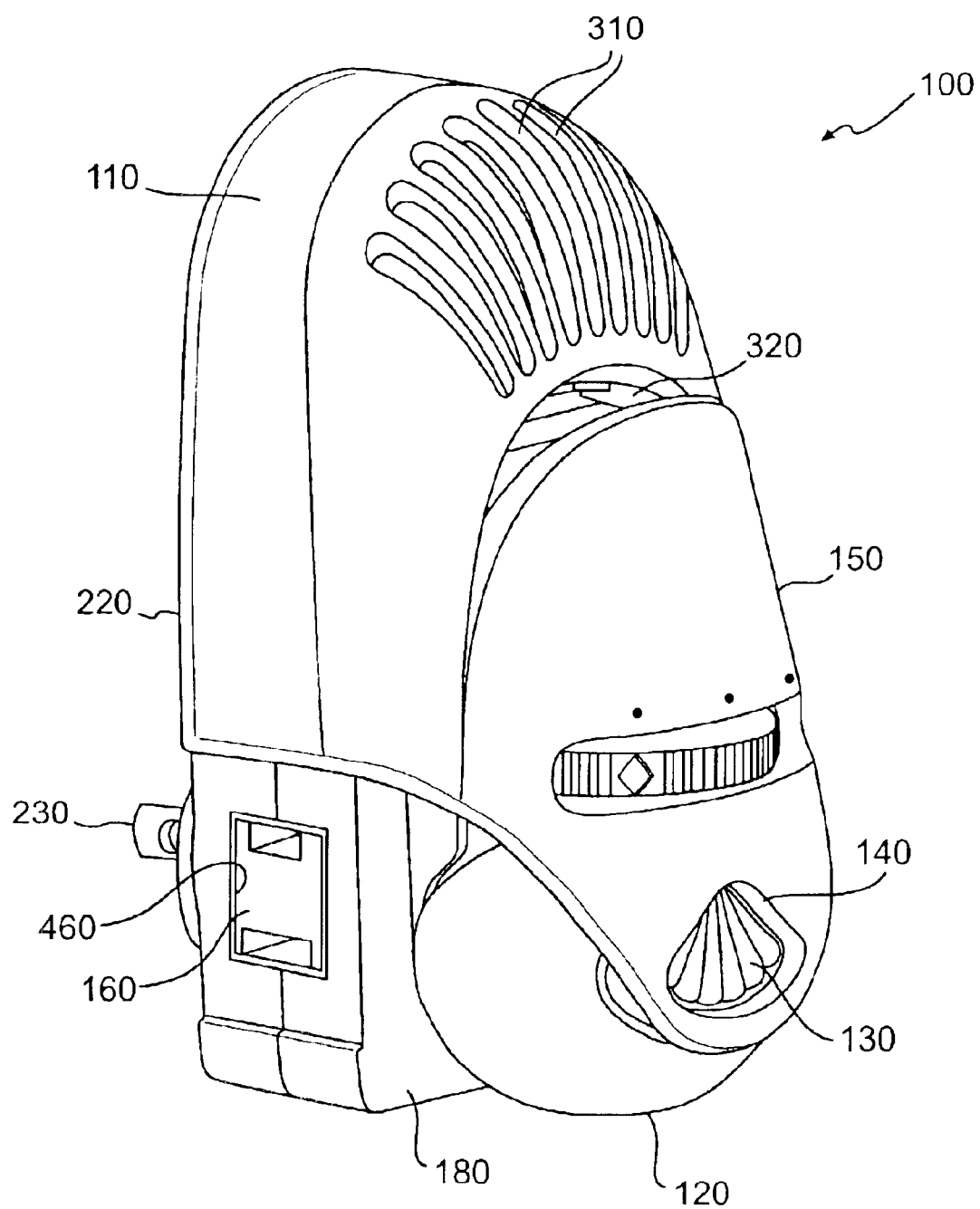
FIG. 1 is a perspective view of a vaporizer incorporating a preferred rotatable plug assembly.

FIGS. 1–7 illustrate a vaporizer 100 incorporating a preferred rotatable plug assembly according to our invention. As shown in FIG. 1, the vaporizer 100 comprises a multi-piece housing 110 in which a bottle 120 is detachably retained. The bottle 120 contains an evaporable substance (not shown), such as, for example, a liquid formulation including a chemical active such as an insecticide, fragrance, odor eliminator, or the like. The term "bottle" is used herein in its broadest possible sense, including any receptacle, container, pouch, etc., capable of holding a liquid formulation. A raised pattern 130 on one side of the bottle is engaged by an opening 140 in a front shell 150 of the vaporizer housing 110, while a similar raised pattern (not shown) on an opposite side of the bottle 120 is engaged by a recess 170 (shown in FIG. 3) in a middle shell 180, in order to secure the bottle 120 within the vaporizer 100. The front shell 150 is sufficiently pliant so that pulling the bottle 120 in a downward direction causes the raised patterns 130 to release from the opening 140 in the front shell 150 and the recess 170 in the middle shell 180, respectively, thereby enabling removal of the bottle 120 from the vaporizer 100. Alternatively, the neck portion of the bottle may be designed to snap or screw into the vaporizer housing. Suitable refill bottles are available in a wide variety of liquid formulations from S.C. Johnson & Son, Inc., of Racine, Wis., under the GLADE® PLUGINS® and RAID® brand names.

Figure 3:
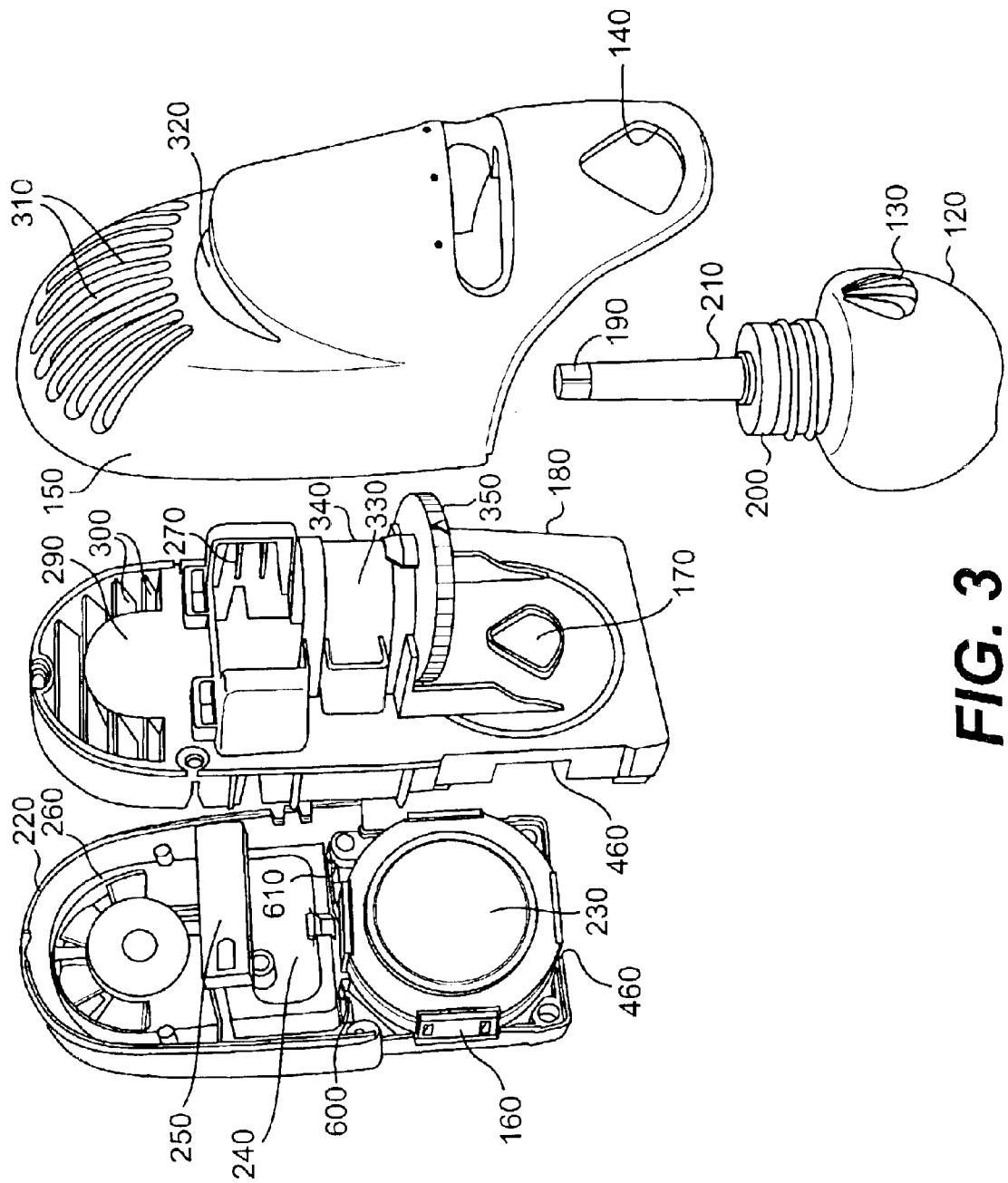
FIG. 3 is an exploded assembly view of the vaporizer shown in FIG. 1.

As shown in FIG. 3, the bottle 120 includes a wick 190 for drawing the liquid formulation out of the bottle 120 and toward an upper portion of the wick 190. A lower portion of the wick 190 is immersed in the liquid formulation, and the upper portion of the wick 190 protrudes above the neck of the bottle 120. Preferably, the wick 190 is positioned within the bottle 120 by a cap 200 which includes a sheath 210 that encases the upper portion of the wick 190, except for an open area near the tip of the wick 190. Alternatively, a cap without a sheath can be utilized. Preferably, the wick is about 7 mm in diameter and is constructed of ultra high molecular weight high density polyethylene.

In the preferred embodiment illustrated in FIGS. 1–7, the vaporizer housing 110 comprises three shells—the front and middle shells 150, 180 noted above and a back shell 220—which are fastened together by heat-staking or any other suitable fastening means, including, for example, rivets, press fit, snap fit, screws, ultrasonic welding, adhesives, or the like. The electrical components (discussed in more detail below) of the vaporizer 100 are housed within the space enclosed by the middle and back shells 180, 220.

Figure 2:
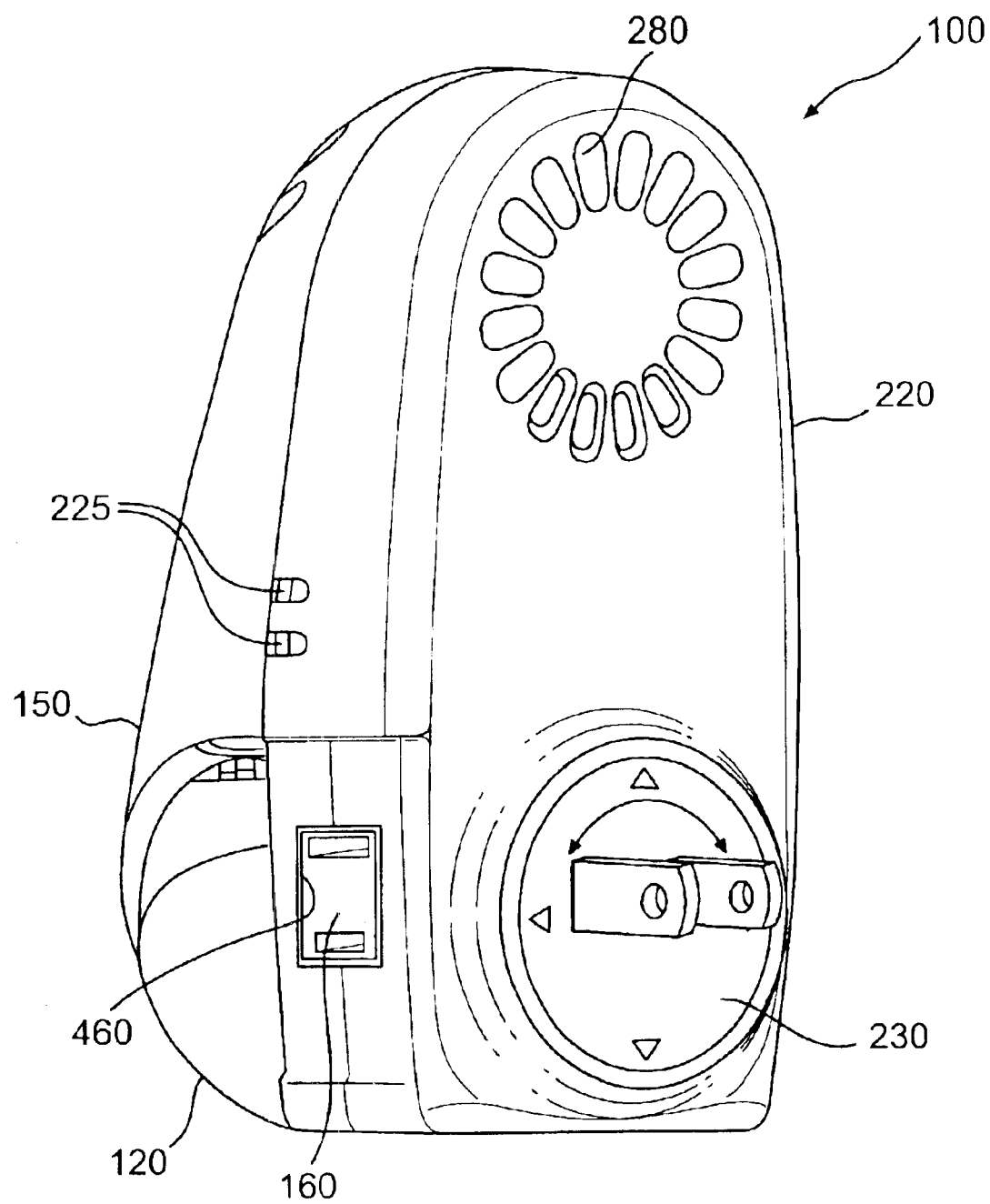
FIG. 2 is a rotated perspective view of the vaporizer shown in FIG. 1.

Referring to FIG. 2, the back shell 220 contains a circular opening in which an electrical plug assembly 230 is seated. The plug assembly 230 serves the dual purpose of supplying power to the electrical components of the vaporizer 100 and also supporting the vaporizer 100 in a wall outlet (not shown). Preferably, the plug assembly 230 is rotatable 360 degrees in order to support the vaporizer 100 in an upright position in both horizontal and vertical polarized wall outlets. Advantageously, the plug assembly 230 can be provided with an extra outlet 160 which is located on the side of the vaporizer 100 when the vaporizer is plugged into a vertical wall outlet (see FIGS. 1 and 5) and on the bottom of the vaporizer 100 when the vaporizer is plugged into a horizontal wall outlet (see FIG. 6).

Figure 4:
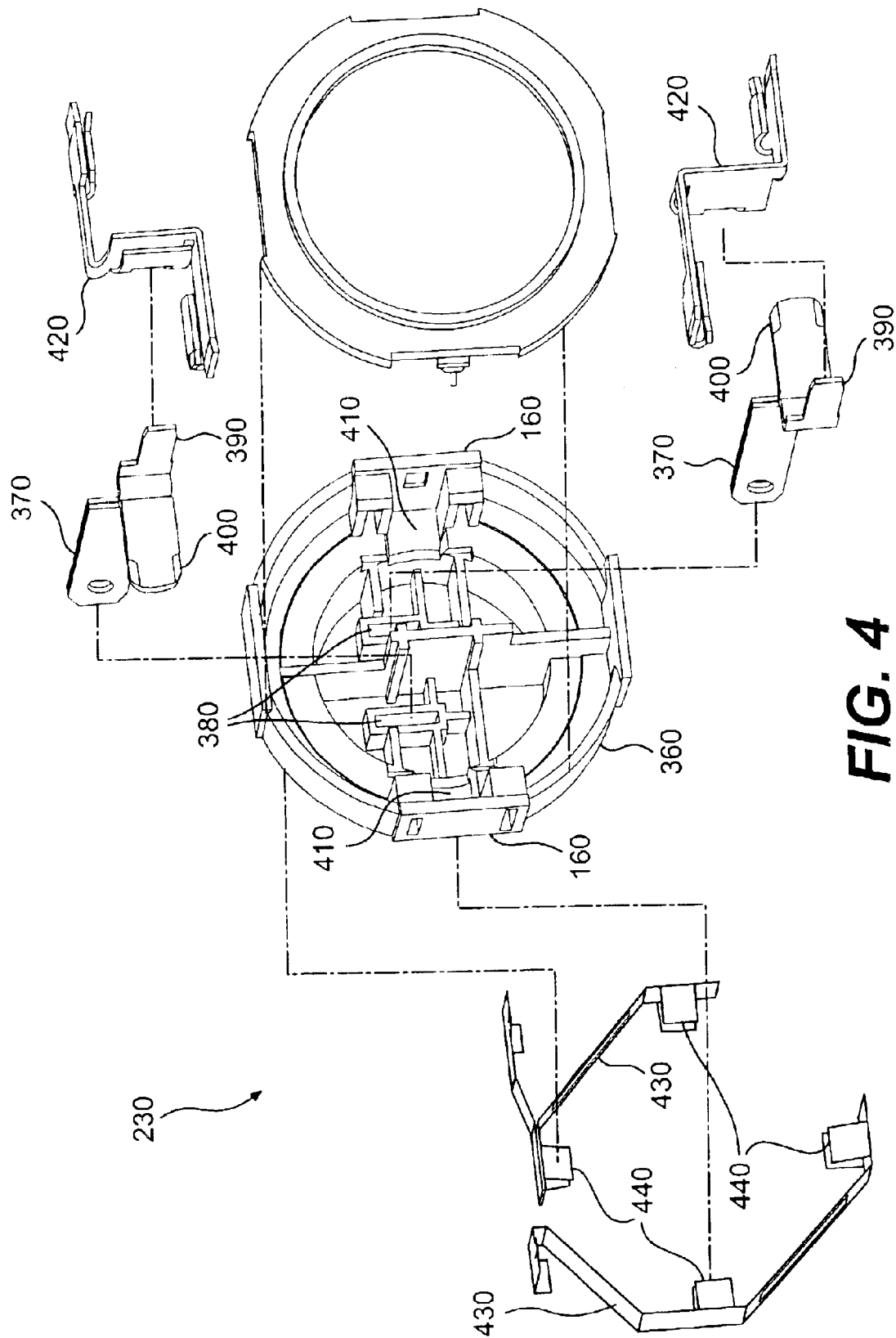
FIG. 4 is an exploded assembly view of the rotatable plug assembly of the vaporizer shown in FIG. 1.
Figure 5:
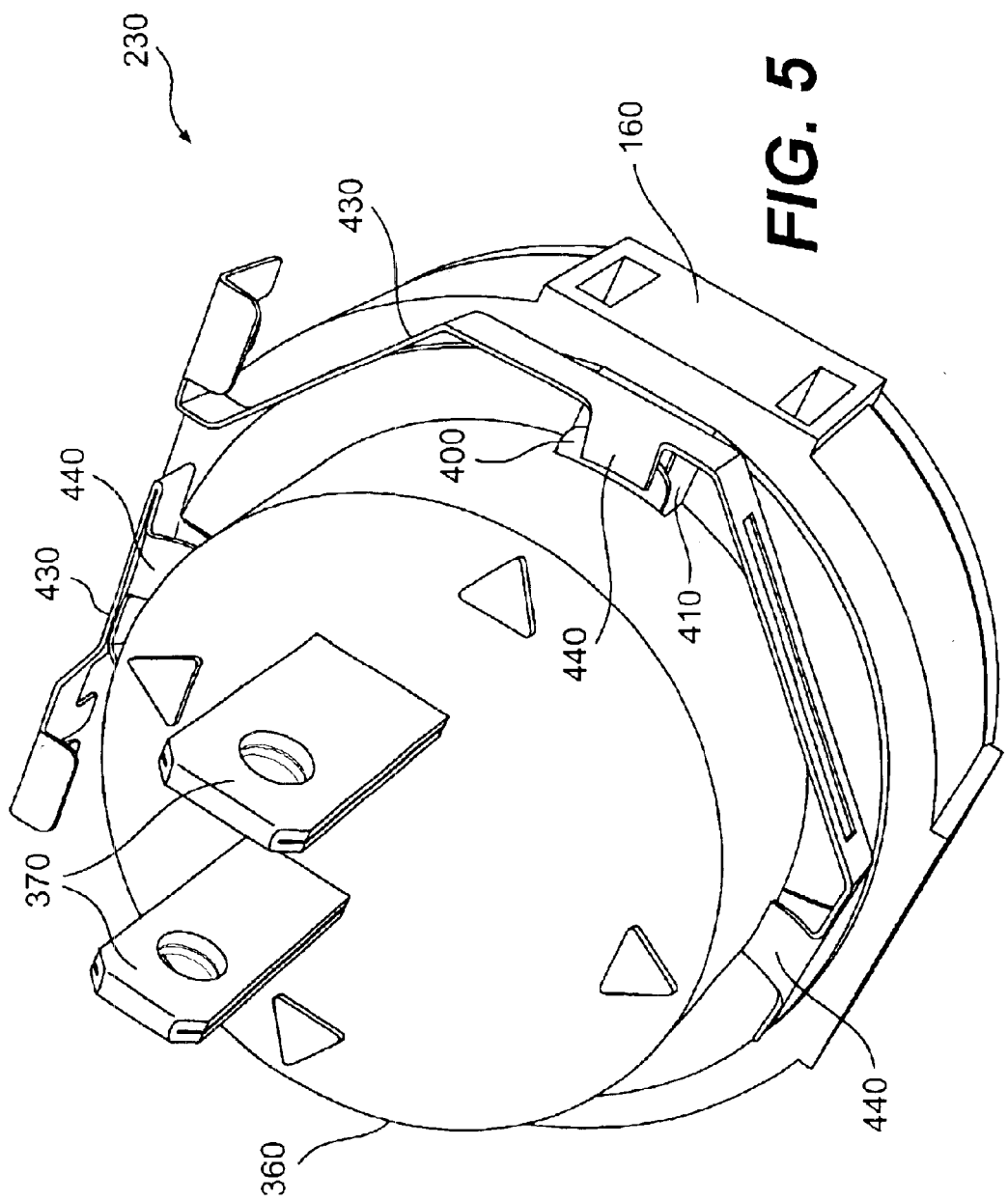
FIG. 5 is a perspective view of the rotatable plug assembly shown in FIG. 4, configured for insertion into a vertical wall outlet.
Figure 6:
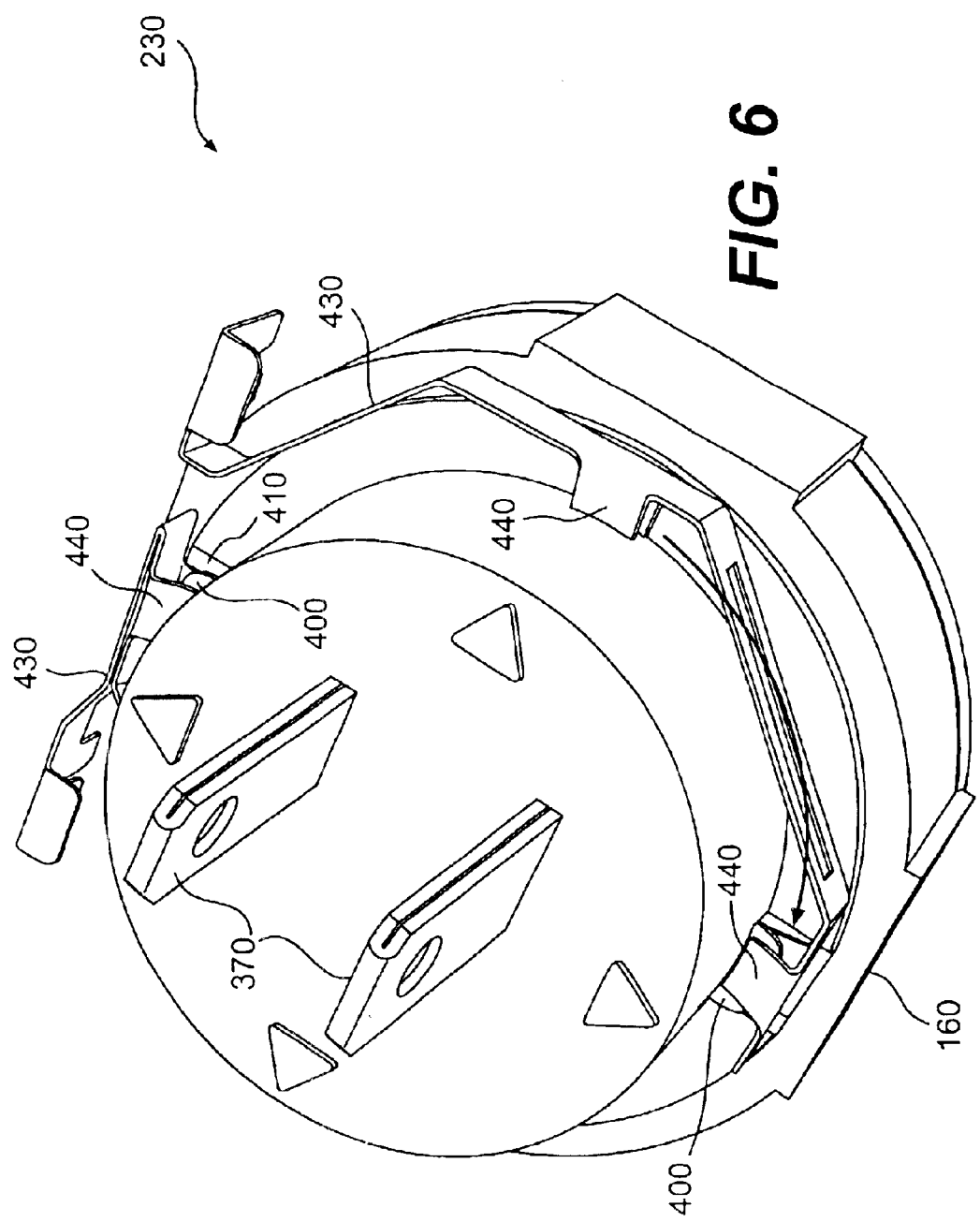
FIG. 6 is a perspective view of the rotatable plug assembly shown in FIG. 4, configured for insertion into a horizontal wall outlet.

As illustrated in FIG. 4–6, the plug assembly 230 comprises a stepped, cylindrically-shaped body 360. Plug blades 370 protrude through narrow slits 380 in the rear face of the plug assembly body 360, in a direction parallel to the axis of rotation of the plug assembly 230. In the preferred embodiment shown, each plug blade 370 includes a spring contact 390 at its distal end and a sliding contact 400. As best illustrated in FIGS. 5 and 6, the sliding contacts 400 protrude slightly through openings 410 provided on opposite sides of the plug assembly body 360. The plug blades 370, including the spring contacts 390 and sliding contacts 400, preferably are made of nickel-plated brass, although other well-known conductive materials could also be utilized.

The plug assembly 230 includes at least one, and preferably two, extra outlets 160. In the preferred embodiment shown, two extra outlets 160 are provided on opposite sides of the plug assembly body 360, spaced approximately 180 degrees apart from each other. A pair of rigid conductive members 420 are press fit over the spring contacts 390, thereby electrically connecting the extra outlets 160 to the plug blades 370. The conductive members 420 do not contact each other. Preferably, the conductive members 420 are made of brass, although other well-known conductive materials could also be utilized.

The plug assembly 230 rotates within a lower portion of the vaporizer housing 110. A pair of contact carriers 430 is fixed within the housing 110, substantially surrounding the cylindrical surface of the plug assembly 230. Preferably, the contact carriers 430 are made of phosphor bronze, but other well-known conductive materials could also be utilized. The contact carriers 430 selectively provide an electrical connection between the plug assembly 230 and the electrical components of the vaporizer 100. In the preferred embodiment shown, the contact carriers 430 include four electrical contacts 440 spaced around the plug assembly 230 approximately 90 degrees apart from each other. Opposing pairs of contacts 440 are sized to receive the sliding contacts 400 of the plug blades 370 at each of four 90-degree intervals of rotation of the plug assembly 230. To facilitate this, the sliding contacts 400 preferably are tapered along their edges, as indicated in FIG. 4. Thus, in the preferred embodiment shown, the plug assembly 230 is capable of conducting power to the electrical components of the vaporizer 100 at each of the four possible 90-degree intervals of rotation of the plug assembly 230. The plug assembly 230 of our invention is capable of being rotated in either direction any number of times, and still will provide the required electrical connections at each 90-degree interval of rotation.

Preferably, the vaporizer housing 110 includes three windows 460—one on the bottom of the vaporizer 100 and one on each side. The windows 460 are positioned such that at least one of the extra outlets 160 is accessible through a window at at least two of the four possible 90-degree intervals of rotation of the plug assembly 230. In the orientation shown in FIG. 5, for example, the extra outlets 160 are aligned with windows 460 on opposite sides of the housing 110, whereas in the rotated orientation shown FIG. 6, only one of the extra outlets 160 is accessible through the window 460 in the bottom of the housing 110. Thus, if the plug assembly 230 includes two extra outlets 160 on opposite sides thereof, at least one of the extra outlets 160 will be accessible at each of the four possible 90-degree intervals of rotation. If there is only one extra outlet, it will be accessible at three of the four 90-degree intervals of rotation.

Alternatively, the vaporizer 100 can have just two windows 460 provided on mutually orthogonal sides of the housing 110, e.g., on the side and bottom. In this case, if the plug assembly 230 includes two extra outlets 160 on opposite sides thereof, one of the extra outlets 160 will be accessible at each of the four possible 90-degree intervals of rotation. If there is only one extra outlet, it will be accessible at two of the four 90-degree intervals of rotation.

Although in the preferred embodiment described above the rotatable plug assembly 230 is incorporated in a liquid vaporizer, those skilled in the art will understand that the plug assembly can be utilized in many different types of wall-mounted, plug-in appliances, such as non-liquid fragrance dispensers, non-liquid insect control devices, night lights, timers, and the like.

The electrical components of the vaporizer 100 alluded to above will now be described with reference to FIGS. 3 and 7. Each contact carrier 430 is electrically connected by a pin 600, 610 to a circuit board 240, which, in turn, is electrically connected to a heating device 250 and, preferably, also to a fan unit 260. The heating device 250 is disposed adjacent to a window 270 in the middle shell 180 which faces the tip of the wick 190 when the bottle 120 is inserted in the vaporizer. Heating the wick 190 enhances the rate at which the liquid formulation evaporates into the surrounding environment, as described more fully below. Preferably, the heating device 250 is a 1.9 k$\Omega$, 7 W metal oxide resistor potted in a ceramic block. The resistor preferably has PTC (positive temperature coefficient) characteristics, meaning that its resistance value increases slightly as the resistor heats up. A suitable resistor is available from Great Land Enterprise Co., Ltd., of Shenzhen, China, for example. Alternatively, the heating device 250 can comprise one or more other types of resistor heaters, a wire-wound heater, a PTC heater, or the like.

The fan unit 260 is disposed within an upper portion of the housing 110. The back shell 220 includes air inlets 280 (shown in FIG. 2) for supplying air to the fan unit 260. As described more fully below, the fan unit 260 creates an airstream that entrains the evaporated liquid formulation and assists in the dispersion of the chemical active into the surrounding environment. Preferably, the flow rate of the fan unit 260 within the vaporizer 100 is approximately 0.5 cubic feet per minute, and the fan speed is approximately 2800–3800 RPM. A suitable fan unit 260 is a 12 V, DC, brushless fan, such as available from Power Logic Tech. Inc., of Tapei-Hsien, Taiwan. Alternatively, other DC or AC fans could be utilized, with appropriate adjustments to the circuit board 240, which is described more fully below.

Figure 7:
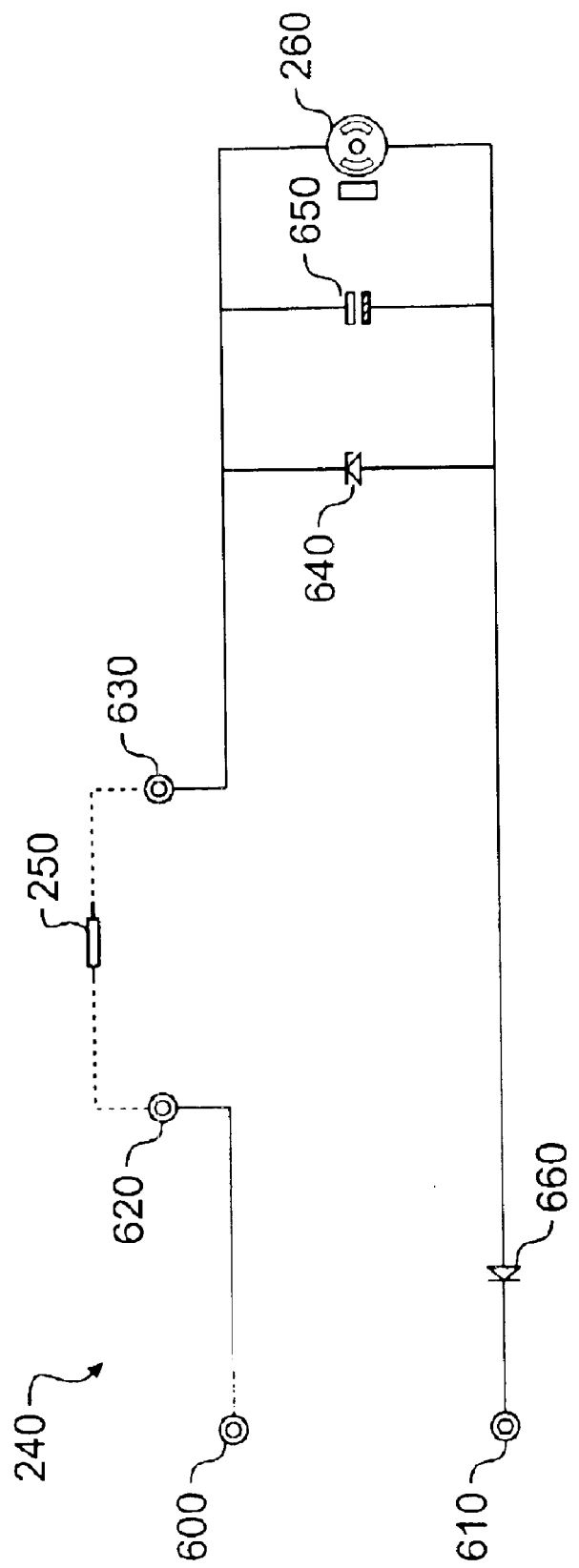
FIG. 7 is a schematic diagram of a preferred electrical circuit for the vaporizer shown in FIG. 1.
Figure 9:
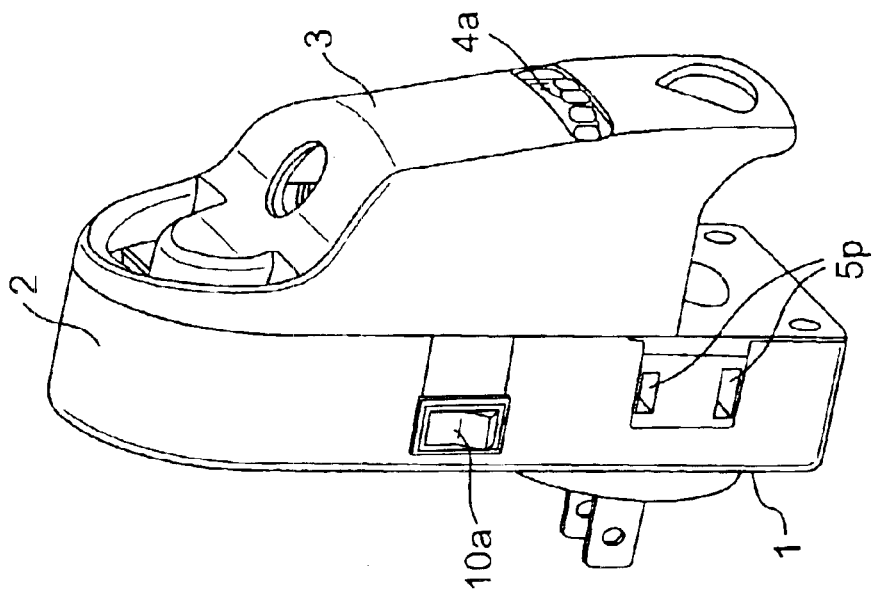
FIGS. 8 and 9 are, respectively, rear and front perspective views of another vaporizer incorporating a preferred rotatable plug assembly.

FIG. 7 is a schematic diagram of a preferred circuit board 240 for the vaporizer 100. Preferably, the circuit board 240 is constructed of a flame-rated material. The pins 600, 610 of the circuit board 240 are provided in electrical contact with the respective contact carriers 430. The voltage applied across the pins 600, 610 is 120 V, at a frequency of 60 Hz. The heating device 250 is connected to the circuit board 240 by a pair of rivets 620, 630. Connected in parallel are (i) a 15 V, 1.3 W Zener diode 640, (ii) a 22 $\mu$F, 50 V aluminum electrolytic capacitor 650, rated for a temperature of 105° C., and (iii) the fan unit 260. The circuit board 240 also includes a 1N 4007 diode 660. The power consumption across the entire circuit is about 3.5 W to about 4.0 W. Those skilled in the art will appreciate that numerous alternative circuit configurations are possible and that values will vary depending on the applied voltage.

Figure 10:
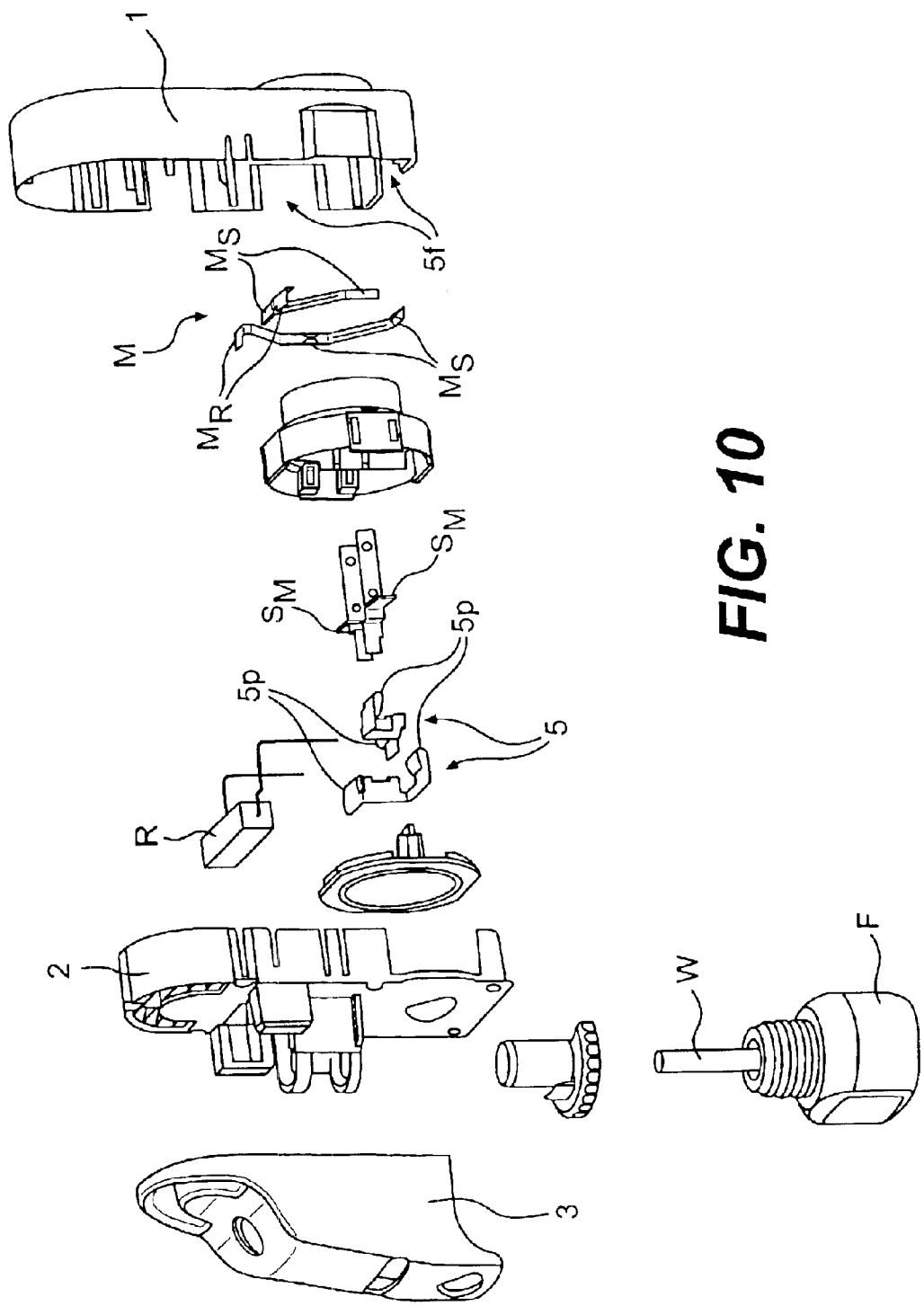
FIG. 10 is an exploded assembly view of the vaporizer shown in FIGS. 8 and 9.

Immediately downstream of the fan unit 260 is a louver structure 290, shown in FIG. 3, comprising at least one louver and, more preferably, a plurality of louvers 300. Preferably, the louver structure 290 is an integral part of the middle shell 150, but it can also be provided separately from the middle shell 150. As illustrated in FIGS. 3 and 10, the louvers 300 are angled upwardly and away from the heating device 250 and the upper portion of the wick 190, preferably at an angle between about 20 degrees to about 60 degrees relative to horizontal when the vaporizer 100 is in an upright position.

The optimum louver angle varies depending on such factors as the fan speed and the air exchange rate within the room in which the vaporizer 100 is located. In rooms with relatively low air exchange rates (e.g., between about 0.6 to about 1.2 exchanges per hour), a louver angle of about 40 degrees to about 45 degrees relative to horizontal is preferred. In rooms with higher air exchange rates, a louver angle of about 25 degrees to about 30 degrees relative to horizontal is preferred.

The middle shell 180 is shaped so as to direct the airstream created by the fan unit 260 through the louvers 300. Notably, the middle shell 180 does not permit stray currents of air to recirculate within the housing 110, where those currents could have an undesirable cooling effect on the heating device 250. A pair of openings 225 (shown in FIG. 2) in the side of the vaporizer 100 helps to achieve proper air circulation through the vaporizer.

The front shell 150 includes a plurality of vents 310 through which the airstream exits the vaporizer 100 after passing through the louvers 300. As the airstream exits the vaporizer through the vents 310, it entrains the evaporated liquid formulation, which rises from the wick 190 through an opening 320 in the front shell 150 below the vents 310.

Optionally, the vaporizer 100 also includes an adjustment mechanism 330 that positions the upper portion of the wick 190 with respect to the heating device 250. Preferably, the adjustment mechanism 330 includes a hollow cylindrical portion 340 that surrounds and engages part of the upper portion of the wick 190, preferably at a location where the wick 190 is encased by the sheath 210. The adjustment mechanism 330 also includes a dial portion 350, accessible from outside the vaporizer housing 110, for rotating the cylindrical portion 340 about an axis of rotation. Rotating the dial portion 350 of the adjustment mechanism 330 causes the wick 190 to move toward or away from the heating device 250 in a lateral direction, i.e., in a direction substantially perpendicular to the longitudinal axis of the wick 190.

Figure 8:
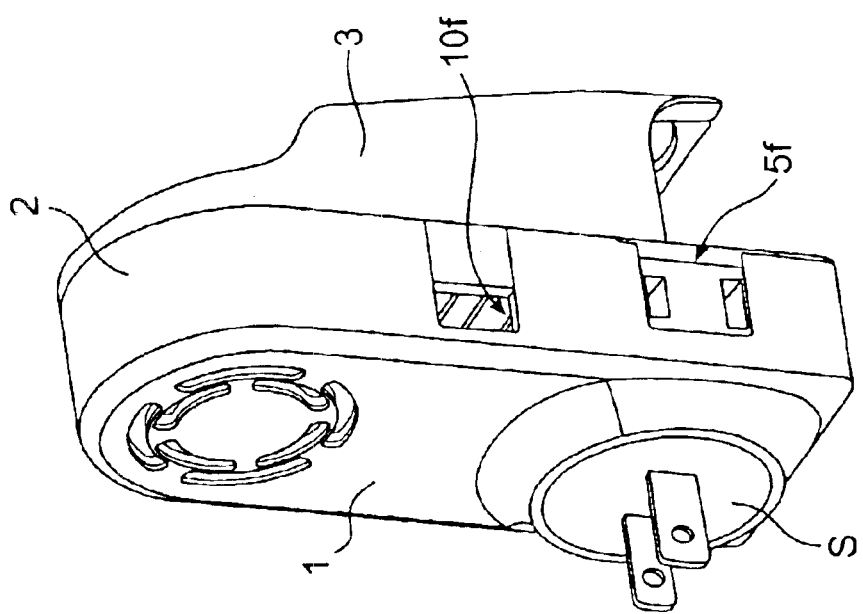

Further preferred embodiments of our invention are illustrated in FIGS. 8–13. In FIG. 8, there is shown a vaporizer including a first shell 1 and a second shell 2 that can be joined together in any well-known manner, including rivets, screws, heat-staking, or the like. The first and second shells 1 and 2 together form the core housing structure of the vaporizer. The housing structure contains many of the basic functional components of the vaporizer, as well as one or more additional functional devices. As shown in FIGS. 8 and 10, basic components of the vaporizer include a rotatable electrical plug assembly S, a contact carrier M having several electrical contacts, an electrical heating device R connected to a pair of contacts $M_R$ of the contact carrier M, a bottle F containing the liquid substance to be evaporated, and a wick W for drawing the liquid substance out of the bottle and toward an upper portion of the wick.

The plug assembly S is of the sliding-contact type and has contacts $S_M$ for engagement with either of two possible corresponding pairs of contacts $M_S$ on the contact carrier M. The pairs of contacts $M_S$ on the contact carrier M are mutually offset by approximately 90 degrees, allowing the plug to be rotated through a range of 360 degrees. This makes the vaporizer easily adaptable for use in both horizontal and vertical electrical outlets, as are found in different parts of the world.

The vaporizer is completed by a cover 3, which preferably surrounds substantially the entire outer surface of the second shell 2 such that substantially only the cover is visible when looking at the vaporizer head-on. The cover 3 is joined to the housing structure, preferably to the second shell 2, by any suitable fastening means. The cover 3 includes one or more access windows corresponding to whatever additional functional device(s) the vaporizer is equipped with. Apart from these minimal functional considerations, the cover design may be tailored to meet consumers' aesthetic preferences.

An advantageous feature of our invention is that it permits any of several different additional functional devices to be incorporated in the vaporizer, without requiring any substantial modification to either the core housing structure or the basic functional components of the vaporizer. To that end, the housing structure, in advance, is configured to receive any of the additional functional devices. The design of the cover 3, meanwhile, can be varied depending on the additional functional device(s) that the vaporizer is equipped with and the aesthetic preferences of a particular market. Additional functional devices for the vaporizer may include, for example, a draft regulator, a wick adjustment mechanism, a fan, a night light, an indicator light, a programmable user interface, or the like.

In the preferred embodiment shown, the vaporizer includes an extra electrical outlet. As shown in FIG. 10, a pair of metal strips 5 is provided within the body of the rotating plug assembly S. One end of each strip 5 is press-fitted into engagement with spring contacts on the pins of the plug, while the other end has a clamping system 5p for connecting to an electrical plug. The extra electrical outlet is accessible via either of two windows 5f provided in the first shell 1, depending on the position assumed by the plug assembly S.

Figure 11:
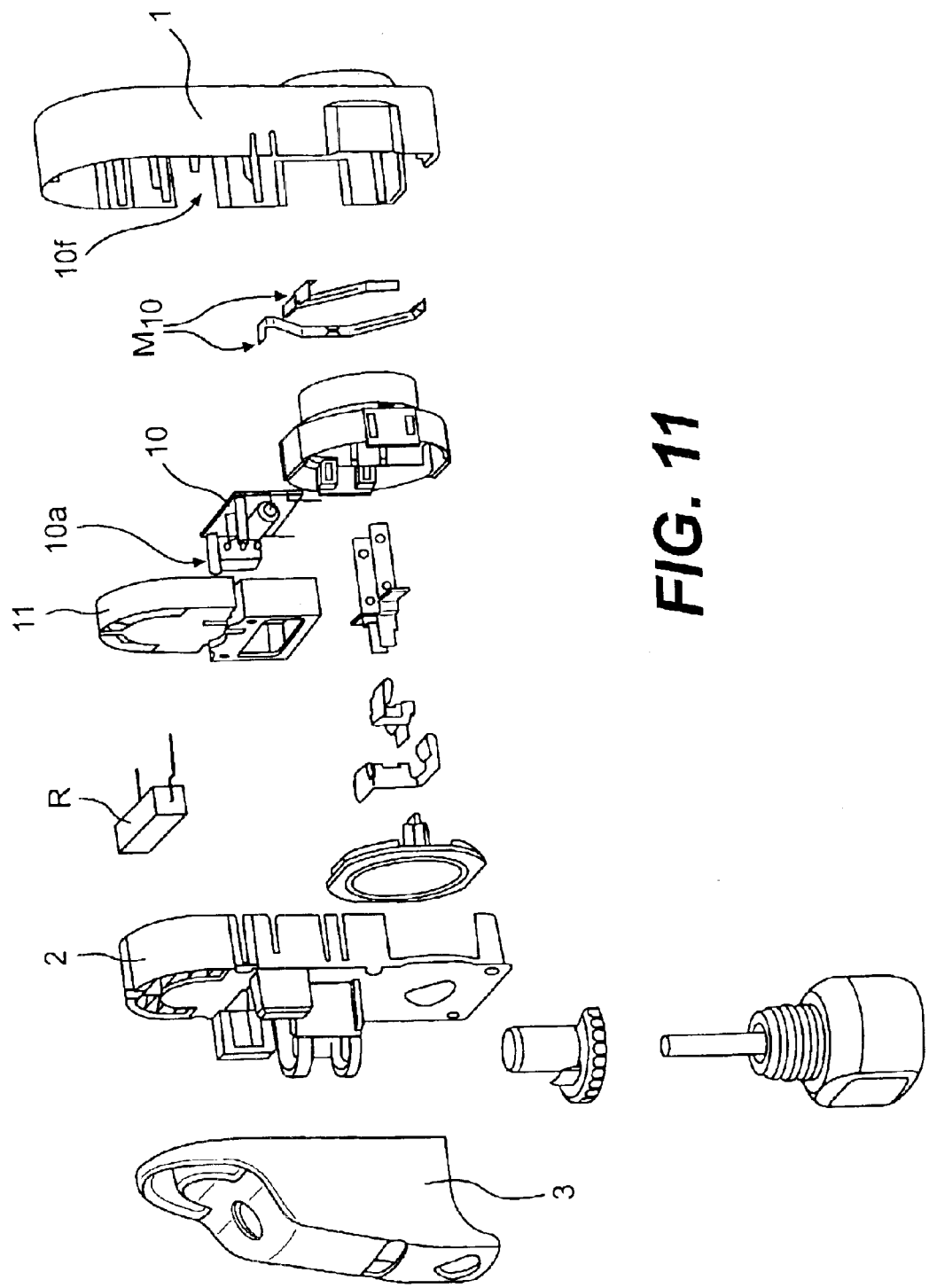
FIG. 11 is a view, similar to that of FIG. 10, in which the vaporizer is provided with a fan.

FIG. 11 illustrates a vaporizer including a fan as an additional functional device. The fan is housed in the top part of the first and second shells 1 and 2, which are provided, for this purpose, with a wide cavity. This cavity houses a printed electrical circuit 10 and a fan assembly 11 that is powered and controlled by the circuit 10. The circuit 10 is in turn powered by means of a pair of contacts $M_{10}$ (which is precisely the same pair of contacts $M_R$ described above in connection with FIG. 10). In this embodiment, the heating device R is connected to the circuit 10 instead of directly to the contact carrier M. The circuit 10 is equipped with a switch 10a that is accessible through a window 10f in the first shell 1.

Figure 12:
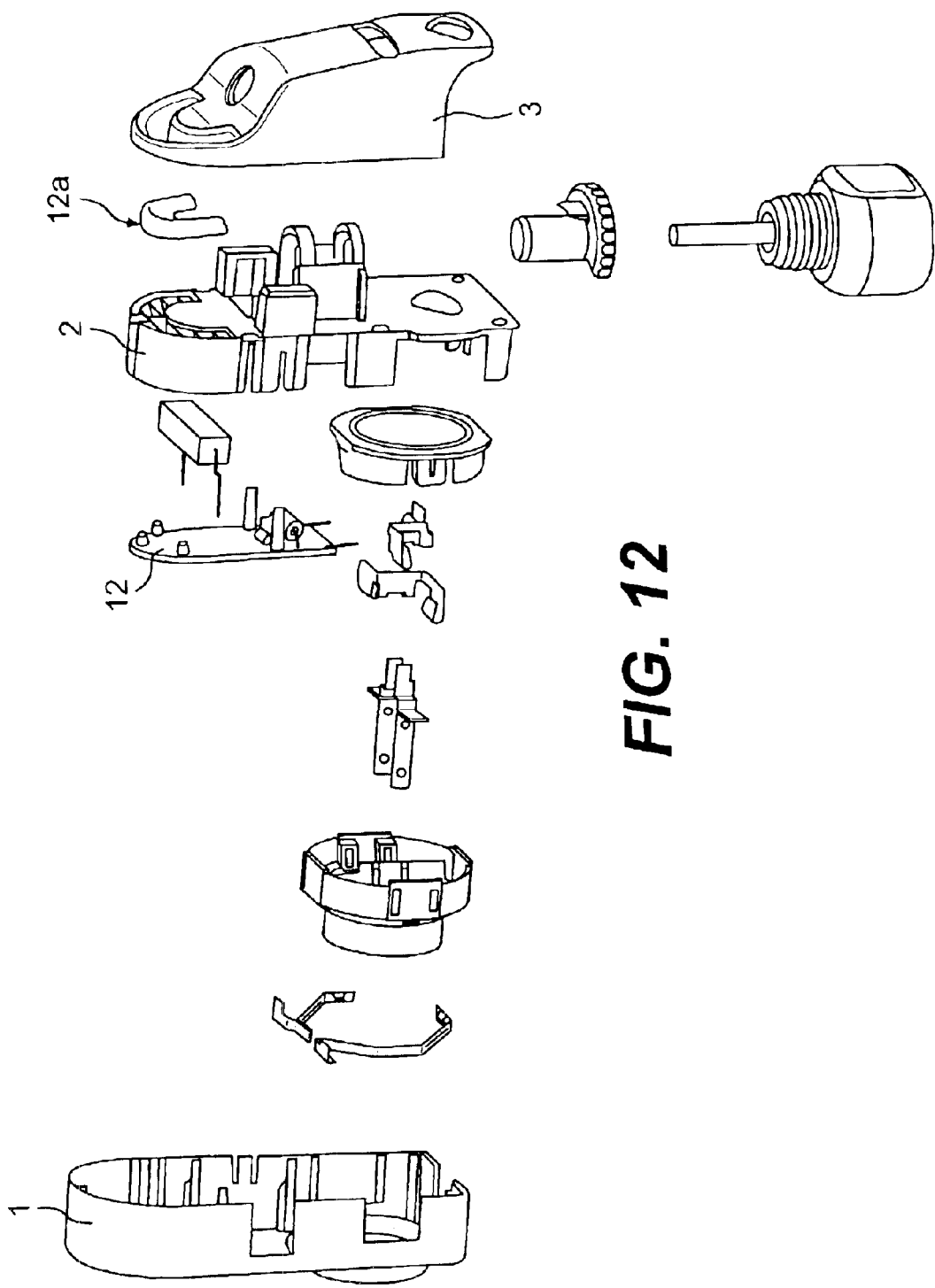
FIG. 12 is a view, similar to that of FIG. 10, but from a different viewpoint, in which the vaporizer is provided with a night light.

FIG. 12 illustrates a vaporizer including a night light 12 as an additional functional device. The night light 12 may be chosen from among various well-known types of commercially-available devices, such as incandescent lamps, neon lamps, LED devices (as shown in FIG. 12), or the like. If desired, a diffusing lens 12a may also be utilized. The electrical connections in this embodiment are identical to those discussed above with respect to FIG. 11.

Figure 13:
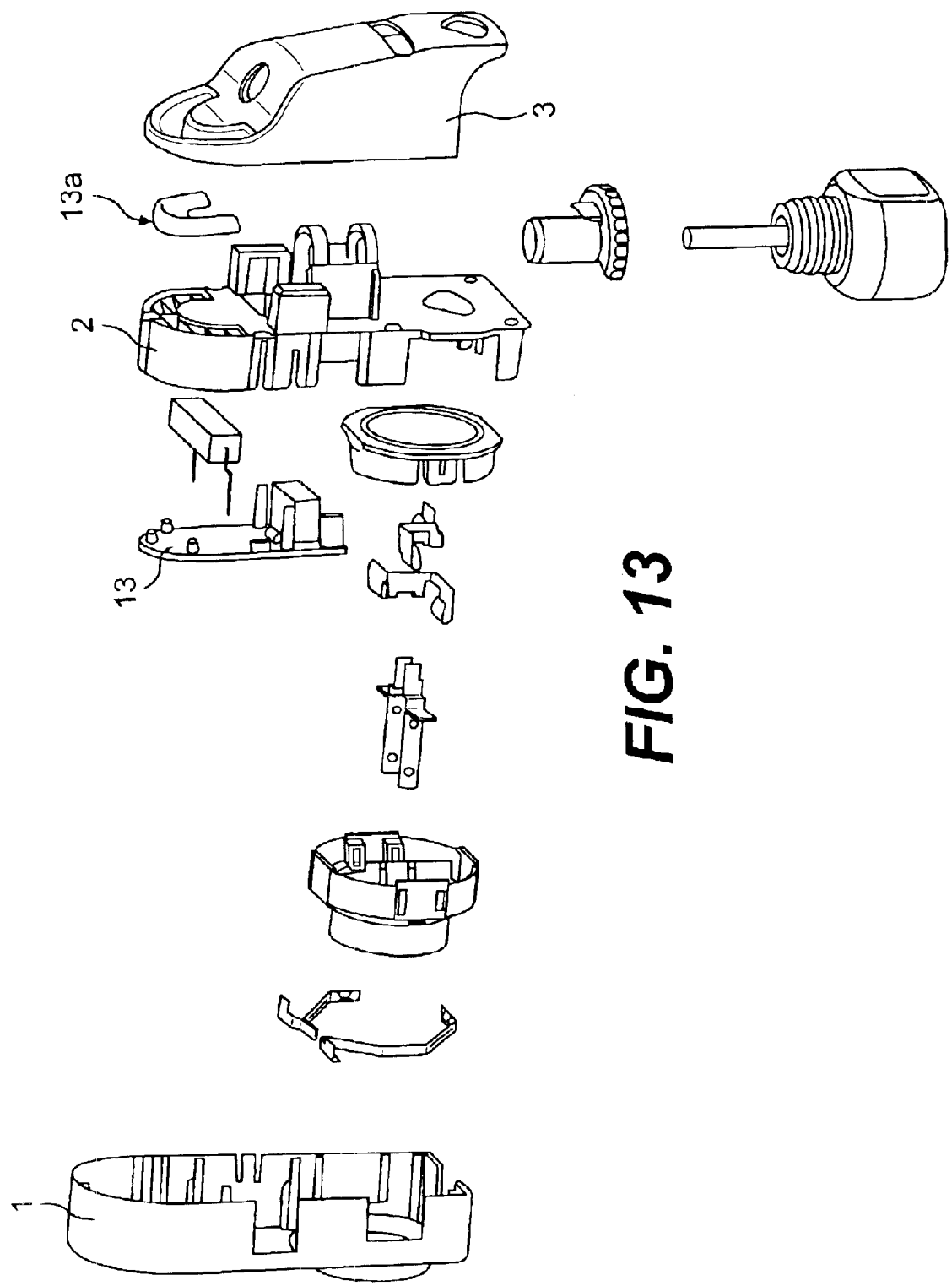
FIG. 13 is a view, similar to that of FIG. 12, in which the vaporizer is provided with an indicator light.

FIG. 13 illustrates a vaporizer including a programmable user interface 13 as an additional functional device. In the preferred embodiment shown in FIG. 13, the interface includes three LED devices. The LED devices preferably have a much lower wattage than those used in the night light embodiment, because they are not intended to provide illumination, but rather only signal the different operating modes of the vaporizer. A diffusing lens 13a may also be used in this embodiment, if desired. The electrical connections in this embodiment are identical to those discussed above with respect to FIG. 11.

From the foregoing description, it should be clear that it is possible to modify the number and type of additional functional devices the vaporizer is equipped with without making any significant modification to its core housing structure, including the first and second shells 1 and 2. Instead, the vaporizer can simply be provided with a cover 3 having the desired aesthetic characteristics and only those access windows that are necessary based on the particular additional functional devices that the vaporizer is equipped with. During manufacture of the vaporizer, the additional functional devices are easily inserted into their respective places and connected to the electrical contacts already provided in the first and second shells 1 and 2.

The embodiments discussed above are representative of preferred embodiments of our invention and are provided for illustrative purposes only. They are not intended to limit the scope of the invention. Although specific structures, components, circuits, etc., have been shown and described, such are not limiting. Modifications and variations are contemplated within the scope of our invention, which is intended to be limited only by the scope of the accompanying claims.

We claim:

1. A wall-mounted, plug-in appliance, comprising:
   a housing containing electrical components of the appliance, the housing including a plurality of windows; and
   a plug assembly rotatably disposed within the housing, the plug assembly including (i) a plug for electrically connecting the plug assembly to a wall outlet and (ii) at least one integral extra outlet to which another electrical appliance can be plugged in,
   wherein the plug assembly conducts power to the electrical components of the appliance at each of at least two 90-degree intervals of rotation of the plug assembly, and the extra outlet is accessible through a respective one of the plurality of windows in the housing at different 90-degree intervals of rotation of the plug assembly.

2. The appliance of claim 1, wherein the electrical components contained in the housing include at least one of a heating device, a fan, a light, and a circuit board.

3. The appliance of claim 1, wherein each of two mutually orthogonal sides of the housing includes a respective one of the plurality of windows, each of the two sides being adjacent and substantially perpendicular to a third side of the housing from which the plug of the plug assembly extends.

4. The appliance of claim 1, wherein a pair of rigid conductive members electrically connects the extra outlet to the plug.

5. The appliance of claim 4, wherein the plug assembly is substantially cylindrical in shape and includes two integral extra outlets spaced approximately 180 degrees apart on the cylindrical surface of the plug assembly.

6. The appliance of claim 5, wherein the pair of rigid conductive members electrically connects each extra outlet to the plug.

7. A wall-mounted, plug-in appliance, comprising:
   a housing containing electrical components of the appliance, the housing including a plurality of windows; and
   a plug assembly rotatably disposed within the housing, the plug assembly including (i) a set of plug blades, extending in a direction parallel to the axis of rotation of the plug assembly, for electrically connecting the plug assembly to a wall outlet, and (ii) at least one integral extra outlet for receiving a set of plug blades of another electrical device, the extra outlet being oriented such that the plug blades of the other electrical device, when inserted into the extra outlet, extend in a direction substantially perpendicular to the axis of rotation of the plug assembly,
   wherein the plug assembly electrically connects the electrical components of the appliance to the wall outlet at each of four 90-degree intervals of rotation of the plug assembly, and the extra outlet is accessible through a respective one of the plurality of windows in the housing at at least two of the four 90-degree intervals of rotation.

8. The appliance of claim 7, wherein the extra outlet is accessible through different ones of the plurality of windows in the housing at at least three of the four 90-degree intervals of rotation.

9. The appliance of claim 7, wherein the electrical components contained in the housing include at least one of a heating device, a fan, a light, and a circuit board.

10. The appliance of claim 7, wherein each of two mutually orthogonal sides of the housing includes a respective one of the plurality of windows, each of the two sides being adjacent and substantially perpendicular to a third side of the housing from which the plug blades of the plug assembly extend.

11. The appliance of claim 7, wherein a pair of rigid conductive members electrically connects the extra outlet to the plug blades of the plug assembly.

12. The appliance of claim 11, wherein the plug assembly is substantially cylindrical in shape and includes two integral extra outlets spaced approximately 180 degrees apart on the cylindrical surface of the plug assembly.

13. The appliance of claim 12, wherein the pair of rigid conductive members electrically connects each extra outlet to the plug blades of the plug assembly.

14. An electrical plug-in device for dispersing a chemical active into a surrounding environment, the device comprising: a housing including a plurality of windows;
at least one electrical component contained within the housing for enhancing dispersion of the chemical active to the surrounding environment; and
a plug assembly rotatably disposed within the housing, the plug assembly including (i) a plug for electrically connecting the plug assembly to a wall outlet and (ii) at least one integral extra outlet to which another electrical appliance can be plugged in,
wherein the plug assembly conducts power to the at least one electrical component at each of at least two 90-degree intervals of rotation of the plug assembly, and the extra outlet is accessible through a respective one of the plurality of windows in the housing at different 90-degree intervals of rotation of the plug assembly.

15. The device of claim 14, wherein the at least one electrical component comprises either a heating device or a fan.

16. The device of claim 14, wherein each of two mutually orthogonal sides of the housing includes a respective one of the plurality of windows, each of the two sides being adjacent and substantially perpendicular to a third side of the housing from which the plug extends.

17. The device of claim 14, wherein a pair of rigid conductive members electrically connects the extra outlet to the plug.

18. The device of claim 17, wherein the plug assembly is substantially cylindrical in shape and includes two integral extra outlets spaced approximately 180 degrees apart on the cylindrical surface of the plug assembly.

19. The device of claim 18, wherein the pair of rigid conductive members electrically connects each extra outlet to the plug.

20. A plug-in vaporizer for dispersing a chemical active into a surrounding environment, the vaporizer comprising:
a bottle containing a liquid formulation including at least one chemical active;
a wick, having a lower portion disposed within the bottle and an upper portion protruding from the bottle, for drawing the liquid formulation from the bottle toward the upper portion of the wick;
a housing in which the bottle is detachably retained, the housing including a plurality of windows;
an electrical heating device, disposed within the housing at a position proximate to the upper portion of the wick, for enhancing evaporation of the liquid formulation from the upper portion of the wick; and
a plug assembly rotatably disposed within the housing for supplying power to the heating device, the plug assembly including (i) a set of plug blades, extending in a direction parallel to the axis of rotation of the plug assembly, for electrically connecting the plug assembly to a wall outlet, and (ii) at least one integral extra outlet for receiving a set of plug blades of another electrical appliance, the extra outlet being oriented such that the plug blades of the other electrical appliance, when inserted into the extra outlet, extend in a direction substantially perpendicular to the axis of rotation of the plug assembly,
wherein the plug assembly electrically connects the electrical components of the appliance to the wall outlet at each of four 90-degree intervals of rotation of the plug assembly, and the extra outlet is accessible through different ones of the plurality of windows in the housing at at least two of the four 90-degree intervals of rotation.

21. The vaporizer of claim 20, wherein the extra outlet is accessible through different ones of the plurality of windows in the housing at at least three of the four 90-degree intervals of rotation.

22. The vaporizer of claim 20, wherein each of two mutually orthogonal sides of the housing includes a respective one of the plurality of windows, each of the two sides being adjacent and substantially perpendicular to a third side of the housing from which the plug blades of the plug assembly extend.

23. The vaporizer of claim 20, wherein a pair of rigid conductive members electrically connects the extra outlet to the plug blades of the plug assembly.

24. The vaporizer of claim 23, wherein the plug assembly is substantially cylindrical in shape and includes two integral extra outlets spaced approximately 180 degrees apart on the cylindrical surface of the plug assembly.

25. The vaporizer of claim 24, wherein the pair of rigid conductive members electrically connects each extra outlet to the plug blades of the plug assembly.

* * * * *